United States Patent
Sinha et al.

(10) Patent No.: US 10,451,599 B2
(45) Date of Patent: Oct. 22, 2019

(54) METHODS OF ISOLATING AND DETECTING METAL IONS FROM PROTEINS

(71) Applicant: Zepto Life Technology, LLC, St Paul, MN (US)

(72) Inventors: Joy Sinha, Inver Grove Heights, MN (US); Gerson Aguirre, Minneapolis, MN (US)

(73) Assignee: ZEPTO LIFE TECHNOLOGY, LLC, St Paul, MN (US)

( * ) Notice: Subject to any disclaimer, the term of this patent is extended or adjusted under 35 U.S.C. 154(b) by 67 days.

(21) Appl. No.: 15/255,756

(22) Filed: Sep. 2, 2016

(65) Prior Publication Data

US 2018/0067094 A1    Mar. 8, 2018

(51) Int. Cl.
*G01N 33/20* (2019.01)
*G01N 33/04* (2006.01)
*G01N 33/84* (2006.01)

(52) U.S. Cl.
CPC .............. *G01N 33/20* (2013.01); *G01N 33/04* (2013.01); *G01N 33/84* (2013.01)

(58) Field of Classification Search
None
See application file for complete search history.

(56) References Cited

U.S. PATENT DOCUMENTS

| | | | |
|---|---|---|---|
| 5,346,999 A | 9/1994 | Cathcart et al. | |
| 8,211,715 B1 | 7/2012 | Royds | |
| 2004/0219695 A1* | 11/2004 | Fox | G01N 27/745 436/526 |
| 2008/0213196 A1 | 9/2008 | Haberlein et al. | |
| 2013/0005594 A1* | 1/2013 | Terbrueggen | C12Q 1/6809 506/9 |

FOREIGN PATENT DOCUMENTS

CN    103674943 A    3/2014

OTHER PUBLICATIONS

Dino-Lite Digital Microscope "Special Application", 5 pgs, taken on Jul. 6, 2015 by Wayback Machine at https://web.archive.org/web/20150706120358/http://www.dinolite.us:80/products/digital-microscopes/usb/special-application (Year: 2015).*
"Reagent" definition by The Free Dictionary 2 pgs, accesed Aug. 21, 2018 (Year: 2018).*
International Search Report and Written Opinion dated Dec. 26, 2017 in International Application PCT/IB2017/055349.
Farag Malhatet al., "Contamination of Cows Milk by Heavy Metal in Egypt," Bull environ Contam Toxicol. 2012; 88:611-613 (doi: 10.1007/s00128-012-0550-x) abstract, p. 612, col. 1, Para. 1.
Naqib Ullah et al., "Estimation of Toxic Metals in Milk Collected from Lactating Mothersin Karak, Khyber Pakhtunkhwa Pakistan" 1JBMSP, 2015; 5(1):24-27, abstract; p. 25, col. 1, Para. 4.
Monsur Ahmad et al., "Contamination of raw fresh milk, market pasteurized milk and powdered milk by toxic heavy metals in Bangladesh," Scientific Research Journal (SCIRJ), Feb. 2016; vol. IV, Issue II, pp. 19-24.
International Preliminary Report on Patentability dated Mar. 14, 2019 in International Application PCT/IB2017/055349.

* cited by examiner

*Primary Examiner* — Thane Underdahl
(74) *Attorney, Agent, or Firm* — Pillsbury Winthrop Shaw Pittman LLP

(57) ABSTRACT

A method of detecting a metal ion in a protein-containing sample includes adding a protein degrading enzyme to the protein-containing sample to form an enzyme degradation product, adding an acid to the enzyme degradation product to provide a mixture, filtering the mixture to provide a supernatant, extracting the supernatant with an organic solvent to remove organic solvent soluble byproducts to provide a washed aqueous layer, and detecting the metal ion in the washed aqueous layer. The method is amenable to the detection of heavy metal ions in complex products such as milk. A kit includes reagents for performing the method.

4 Claims, 4 Drawing Sheets

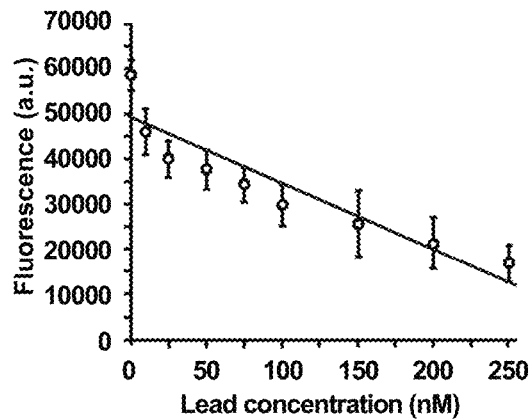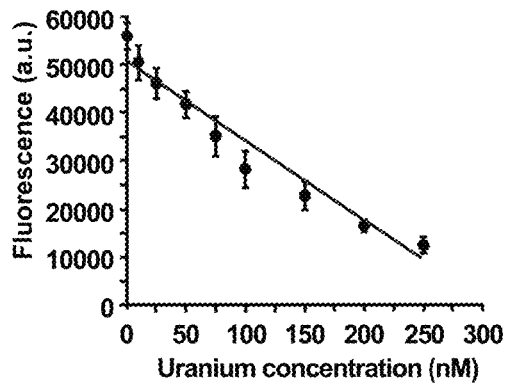
FIGURE 7A  FIGURE 7B
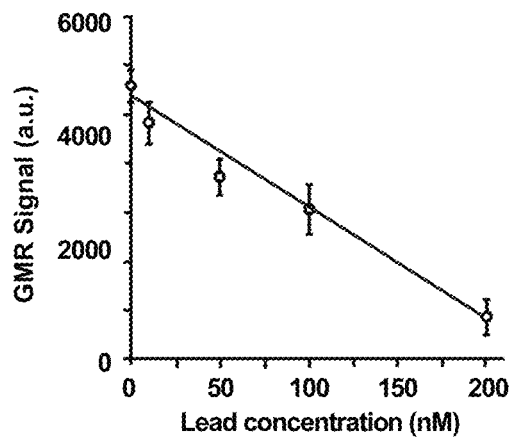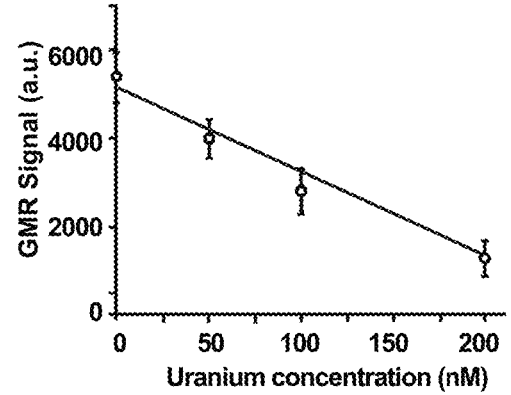
FIGURE 8A  FIGURE 8B

US 10,451,599 B2

METHODS OF ISOLATING AND DETECTING METAL IONS FROM PROTEINS

BACKGROUND

The present disclosure relates to metal ion isolation and detection. More particularly, the present disclosure relates to methods for isolation and detection of metal ions from proteins.

Metals (as part of compounds or as ions), including heavy metals, are pollutants gaining more attention due to potential toxicity which can have lethal effects on living systems and general health. One source of exposure to such metals is food, in particular dairy products such as milk. Detection and monitoring of metals is highly desirable, in view of continuing incidences of contaminated milk products in several parts of the world.

Existing technologies to detect metals, heavy metals in particular, are expensive, time-consuming or use large (or bulky) devices that require a specialized laboratory and make their use for field detection impractical.

Milk presents a typical example of interest for the metal detection problem, in foodstuff. Milk is an emulsion or colloid of butterfat globules within an aqueous solution. The exact components of raw milk may vary but in general it contains significant amounts of lactose, fat, proteins and minerals as well as vitamins. The composition creates a significant problem for field assay detection techniques because such field devices typically rely on biomolecule-based assays employing DNA, RNA or proteins. A complex matrix such as milk can create significant interference and may require time-consuming sample preparation.

Thus, there is a need to provide improved solutions for isolation and detection of metal ions from complex protein-containing substrates, such as milk, that avoid the above-mentioned drawbacks. The present disclosure provides new methods to address these and related issues.

SUMMARY

In some aspects, embodiments herein relate to methods of detecting a metal ion in a protein-containing sample comprising adding a protein degrading enzyme to the protein-containing sample to form an enzyme degradation product, adding an acid to the enzyme degradation product to provide a mixture, filtering the mixture to provide a supernatant, extracting the supernatant with an organic solvent to remove organic solvent soluble byproducts to provide a washed aqueous layer, and detecting the metal ion in the washed aqueous layer.

In some aspects, embodiments herein relate to methods of detecting a heavy metal ion in a milk sample comprising adding a proteinase K enzyme to the milk sample to form an enzyme degradation product, adding nitric acid to the enzyme degradation product to provide a de-emulsified mixture, filtering the de-emulsified mixture to provide a supernatant, extracting the supernatant with chloroform to remove chloroform soluble byproducts to provide a washed aqueous layer, and detecting the heavy metal ion in the washed aqueous layer.

In some aspects, embodiments herein relate to kits comprising a container for holding a protein-containing sample, a proteinase K reagent, a nitric acid reagent, a chloroform reagent, and instructions for performing the isolation of metal ions from the protein-containing sample.

BRIEF DESCRIPTION OF DRAWINGS

Various embodiments of the present disclosure will be described herein below with reference to the figures wherein:

FIG. 7A shows a plot of lead (II) concentration (nM) versus fluorescence (a.u.) from samples isolated from milk indicating the ability to quantitatively detect lead.

FIG. 7B shows a plot of uranium (VI) concentration (nM) versus fluorescence (a.u.) from samples isolated from milk indicating the ability to quantitatively detect uranium.

FIG. 8A shows a plot of lead (II) concentration (nM) versus GMR signal (a.u.) from samples isolated from milk indicating the ability to quantitatively detect lead.

FIG. 8B shows a plot of uranium (VI) concentration (nM) versus fluorescence (a.u.) from samples isolated from milk indicating the ability to quantitatively detect uranium.

DETAILED DESCRIPTION

Figure 1:
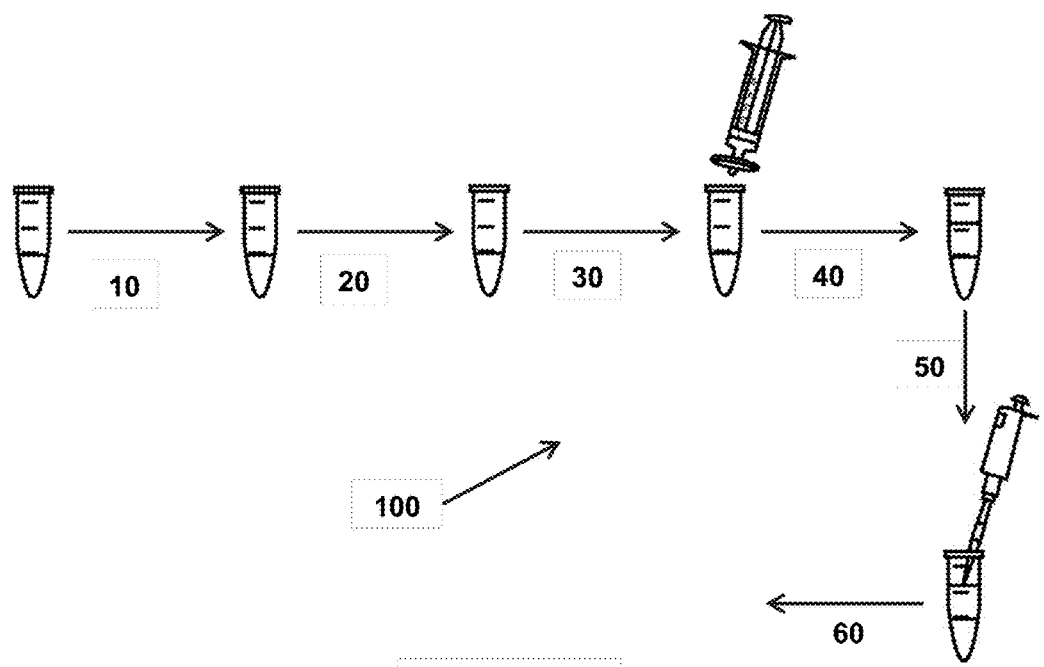
FIG. 1 shows a method for the isolation and detection of metal ions from a protein-containing sample, in accordance with embodiments herein.

Embodiments herein provide processes for isolating metals, including heavy metals from protein-rich substrates, such as from milk. In an exemplary method isolating heavy metals from milk in the Examples below, three facile steps are used to remove interfering proteins and lipids. In some such embodiments, the first step may employ an enzyme to degrade the proteins in the milk. In the second step, acid is added to de-emulsify the milk. In the third step, a nitrocellulose filter is used to bind the remaining proteins, lactose and fat. These three steps may be generally used in a methodology to facilitate detection of metal ions from protein sources and foodstuffs, more generally. This process is simple, avoids use of any specialized laboratory instrument and is rapid with a timescale for detection in a range from about 45 to about 60 minutes total. Additional reagents, such as anionic surfactants, may be employed to accelerate the detection time by increasing the rate of the enzyme degradation step in the processes disclosed herein.

The methods herein are general and are exemplified herein in the detection of two different heavy metal ions (lead and uranium) in milk. The isolated metal ions can be quantitatively detected using any bioassay. The bioassays for the actual detection step are not limited. For example, one can use traditional fluorescence detection methods or a giant magnetoresistance (GMR) platform, as disclosed in pending U.S. Application Publication No. 2016/0011182, which is incorporated herein by reference in its entirety. Other detection methods include colorimetric methods, such as with horseradish peroxidase, chemiluminescence, or electrochemical methods.

In some embodiments, there are provided methods of detecting a metal ion in a protein-containing sample comprising adding a protein degrading enzyme to the protein-containing sample to form an enzyme degradation product, adding an acid to the enzyme degradation product to provide a mixture, filtering the mixture to provide a supernatant, extracting the supernatant with an organic solvent to remove organic solvent soluble byproducts to provide a washed aqueous layer, and detecting the metal ion in the washed aqueous layer.

In some embodiments, any one of the aforementioned steps in the method may be omitted depending on the nature of the protein-containing sample. For example, in some embodiments, it may be possible to omit adding the acid to the enzyme degradation product. While this step is useful in the example of milk as an aid to de-emulsify the milk, other samples may not require such treatment because they may not be emulsions to begin with or the protein-degrading enzyme may be sufficient to break down the protein-containing sample to cause de-emulsification on its own. In other embodiments, the protein degrading enzyme may be omitted. In such embodiments, treatment of a protein-containing sample with strong acids, such as concentration nitric acid, may be sufficient. Thus, in some embodiments, there are provided methods that do not employ a protein degrading enzyme. In some such embodiments, the methods do not employ a proteinase K. In other embodiments, the methods do not employ a strong acid.

In some embodiments, the protein-containing sample is liquid milk. In other embodiments, the protein-containing sample is powdered milk. In still further embodiments, the protein-containing sample is a solution of a protein powder. Thus, methods herein can be used to detect metals, including heavy metals, in a variety of consumer products, including but not limited to protein supplements and related nutraceuticals. In some embodiments, methods disclosed herein are particularly suited to the detection of metals in dairy products including, without limitation, butter, milk, cheese, crème, yogurt, sour cream, whey products, evaporated milk, buttermilk, infant formula products, milk protein concentrates, milk hydrolysates, and caseinates. The protein-containing sample is not limited to dairy-based products, with the methods being amenable to metal detection in plant and nut-based milks as well, including milks derived from soy, almonds, hazelnuts, cashews, and the like.

In some embodiments, the protein degrading enzyme may be a proteinase K enzyme. Other protein degrading enzymes may be used alone or in combination with proteinase K including, without limitation, pserine proteases, threonine proteases, cysteine proteases, aspartic proteases, and glutamic proteases. Other protein degrading enzymes may include, without limitation, digestion enzymes such as pepsin, trypsin, chymotrypsin, metalloprotease, and elastase.

In embodiments, methods may further include the use of a denaturing agent. The denaturing agent may be particularly beneficial added during the initial protein degrading step with the protein degrading enzyme. Without being bound by theory, the denaturing agent may provide a more open protein structure facilitating access by the protein degrading enzymes. In such embodiments, the denaturing agent may be an anionic or non-ionic surfactant, urea, a chelating agent, a sulfhydryl reagent, a serine protease, or combinations thereof.

Anionic or non-ionic surfactants may include one or more of ammonium lauryl sulfate, potassium lauryl sulfate, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium stearate, and the similar anionic surfactants. Non-ionic surfactants may include Tween-20.

In some embodiments, the methods may include a second step that is a strong acid treatment step. In some such embodiments, the acid may be concentrated nitric acid. In other embodiments, the acid may be hydrochloric acid or an acid buffer such as sodium acetate. The concentration of the acids may be about 1M whereas the acid buffers may be about 3M.

In some embodiments, the filtering step is performed with about a 0.2 micron ($\mu$m) pore size filter, although a range of sizes from about 0.05 $\mu$m to about 1 $\mu$m may be useful. In some embodiments, the filter may be a nitrocellulose filter or a membrane that efficiently bind protein (e.g. silicon membrane).

In embodiments, the detecting step is performed by fluorescence detection. In other embodiments, the detecting step is performed by giant magnetoresistance (GMR) measurements. In some embodiments, the detecting step may be performed by colorimetric methods or with electrochemical sensors. The Examples below show the use of these detection methods in practice.

U.S. Application Publication No. 2016/0011182 describes the use of GMR in a magnetic sensor having one or more layers formed on a base for sensing a magnetic field created by magnetic particles present in proximity to the magnetic sensor. A first end of each of a first set of strands (designed DNA or RNA that is query metal ion selective) is immobilized with respect to the magnetic sensor. A magnetic particle is attached to a second end of each of the first set of strands so that when a sample containing a query metal ion is in contact with the base, the query metal ion causes at least some of the first set of strands to break resulting in the magnetic particle attached to the second end of each of the at least some of the first set of strands to no longer be in proximity to the magnetic sensor. The change can be measured with an appropriate interface of the detection device. In some embodiments, other conventional GMR detection motifs may be used.

In some embodiments, there are provided methods of detecting a heavy metal ion in a milk sample comprising adding a proteinase K enzyme to the milk sample to form an enzyme degradation product adding nitric acid to the enzyme degradation product to provide a de-emulsified mixture filtering the de-emulsified mixture to provide a supernatant, extracting the supernatant with chloroform to remove chloroform soluble byproducts to provide a washed aqueous layer, and detecting the heavy metal ion in the washed aqueous layer.

Referring now to FIG. 1, there is shown a schematic diagram of an exemplary method 100 for detecting heavy metal ions in a milk sample in step 10 the sample is incubated with a proteinase K enzyme to degrade the proteins. Nitric acid (concentrated) may be added at step 20. This may serve to both de-emulsify and further denature the degraded enzyme from step 10. At step 30, the sample is then passed through a filter, such as a nitrocellulose filter. Chloroform or other suitable organic solvent for bilayer extraction is then added and thoroughly mixed at step 40. At step 50 the aqueous layer containing the query heavy metal ion is separate from the organic layer. Finally, at step 60 the aqueous layer is tested to detect the query heavy metal ion.

This last step can be performed in any manner enumerated herein, including by fluorescence detection or GMR measurements.

In some embodiments, the heavy metal ion is lead. In some embodiments, the heavy metal ion is uranium. In some embodiments, the methods for detecting heavy metal ions in milk are designed to detect with selectivity for particular heavy metal ions. In some embodiments, the detecting methods may be designed to detect two or more heavy metal ions simultaneously, such as two, three, four, or even five heavy metal ions.

In some embodiments, there are provided kits comprising a container for holding a protein-containing sample, a proteinase K reagent, a nitric acid reagent, a chloroform reagent and instructions for performing the isolation of metal ions from the protein-containing sample. In some embodiments, the kit is a small scale kit for performing the isolation of metal ions in the field. In some embodiments, kits may further comprise a hand held detection device for detecting metal ions. In some such embodiments, the hand held detection device may employ fluorescence detection or detection based on giant magnetoresistance (GMR).

The kits may further comprise other protein denaturing agents, including at least one selected from the group consisting of sodium dodecyl sulfate (SDS), urea, ethylene-diamine tetraacetic acid, trypsin, and chymotrypsin. Kits may also contain the requisite buffers, vials of deionized water, and other reagents.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

This example describes an exemplary method for isolating heavy metals from milk and detection by fluorescence and with a magnetic sensor.

Digestion of Proteins

The main biomolecular components in milk and milk-based products are proteins and lipids. They are also responsible for interference with most bioassays. To remove proteins, this Example employs a protein digesting enzyme. Although there are many such protein digesting enzymes that are potentially useful, this Example uses Proteinase K. Proteinase K is active under a diverse set of conditions, works at room temperature and does not need any special buffer. It is also a common enzyme in biochemistry, especially where removal of proteins are required without altering DNA or RNA (e.g., genomic DNA extraction from bacterial cells). Proteinase K digestion time can vary. The minimum time required may be about 15 minutes in the presence of about 90 units of proteinase K in milk at room temperature.

Choice of Acid

Figure 2:
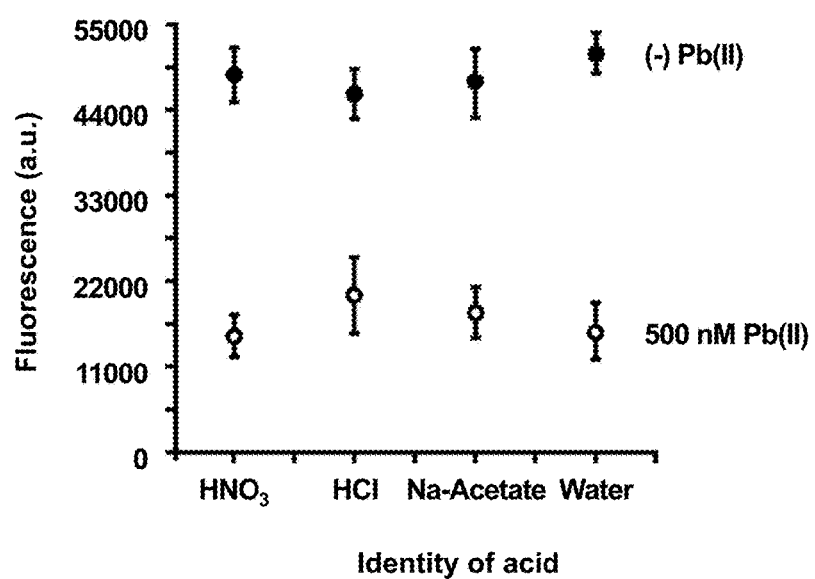
FIG. 2 shows a plot indicating the effectiveness of the acid on extraction of lead ion from milk via fluorescence detection.

To optimize the process in milk, several acids to de-emulsify the milk were tested, including nitric acid (1M), hydrochloric acid (1M) and a low pH sodium acetate buffer (3M, pH 5.2). The volume used for all trials was 167.5 microliters. The results indicated that presence of $Pb^{2+}$ ion can be detected with both acids and sodium acetate buffer. FIG. 2. shows the effect of acid on extraction of lead ion from milk. Closed circles indicate DNAzyme-based sensor's fluorescence signal in the absence of lead and open circles indicate fluorescence signal obtained in the presence of 500 nM $Pb^{2+}$. As a control, DNAzyme-based sensor was used to detect lead ion in water where no extraction from milk was involved. This result provided a control and was used to assess the effectiveness of the extraction protocol. When compared to just water, which acted as a control, nitric acid showed the best result. Therefore, for further experiments, nitric acid was acid employed. It is expected that sulfuric acid would work in this step just as well.

Choice of Organic Solvent for Extraction

Even after the milk is de-emulsified and passed through a nitrocellulose filter, it was expected that there would be residual proteins and lipids in the filtrate. In biochemistry, to remove trace amount of proteins from nucleic acid solution, organic solvents are often used. A classic example is phenol chloroform extraction of DNA or RNA after enzymatic process. In this process, the proteins denature in organic solvents and settle in the interface of aqueous and organic layers. The salts and nucleic acids remain in aqueous layer. Since lipids are soluble in non-polar organic solvents, it was hypothesized that an organic solvent extraction will also remove the lipids. Organic solvents that can be employed include, without limitation, chloroform, ethyl acetate, and a mixture of phenol-chloroform-isoamyl alcohol.

Figure 3:
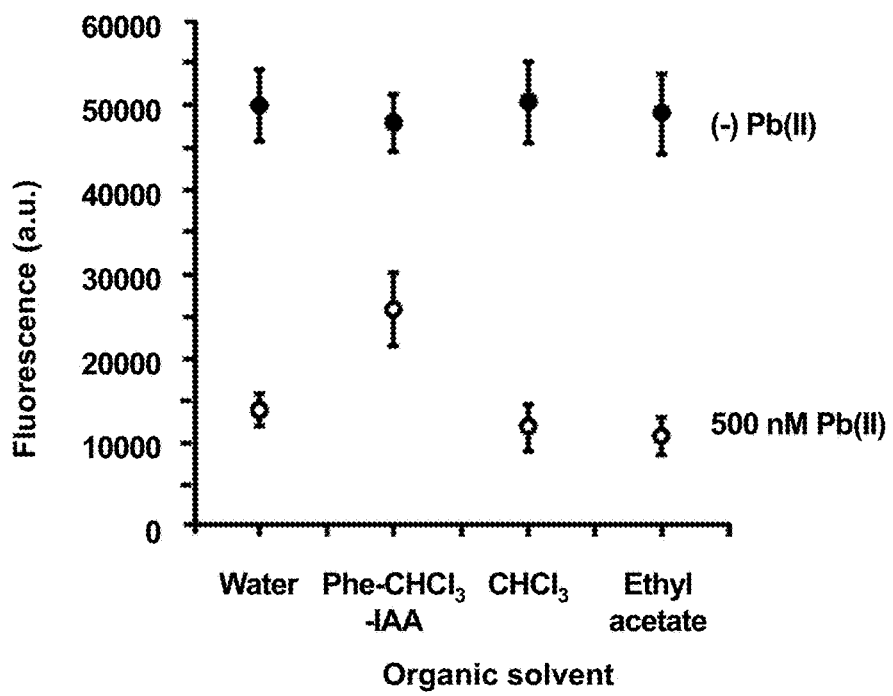
FIG. 3 shows a plot indicating the effectiveness of the organic solvent on extraction of lead ion from milk via fluorescence detection.

FIG. 3 shows the effect of organic solvent on extraction of lead ion from milk. Closed circles indicate fluorescence signal obtained in the absence of lead, whereas open circles indicate fluorescence signal obtained in the presence of 500 nM $Pb^{2+}$. Phe-CHCl3-IAA is phenol-chloroform isoamyl alcohol mixture; $CHCl_3$ is chloroform. As noted in FIG. 2, the result in water was used as a control and to assess the effectiveness of the extraction protocol.

For phenol-chloroform-isoamyl alcohol, phase separation required centrifugation. Additionally, the result showed suboptimal activity after extraction. For ethyl acetate and chloroform, phase separation can be achieved without centrifugation. Both chloroform and ethyl acetate showed the expected level of activity. However, chloroform was determined to be the most user-friendly as the aqueous layer is the top layer and thus easy to remove from the organic layer. For ethyl acetate, the aqueous layer is the bottom layer and thus its removal may be tricky for a non-expert person.

Choice of Filter

Figure 4:
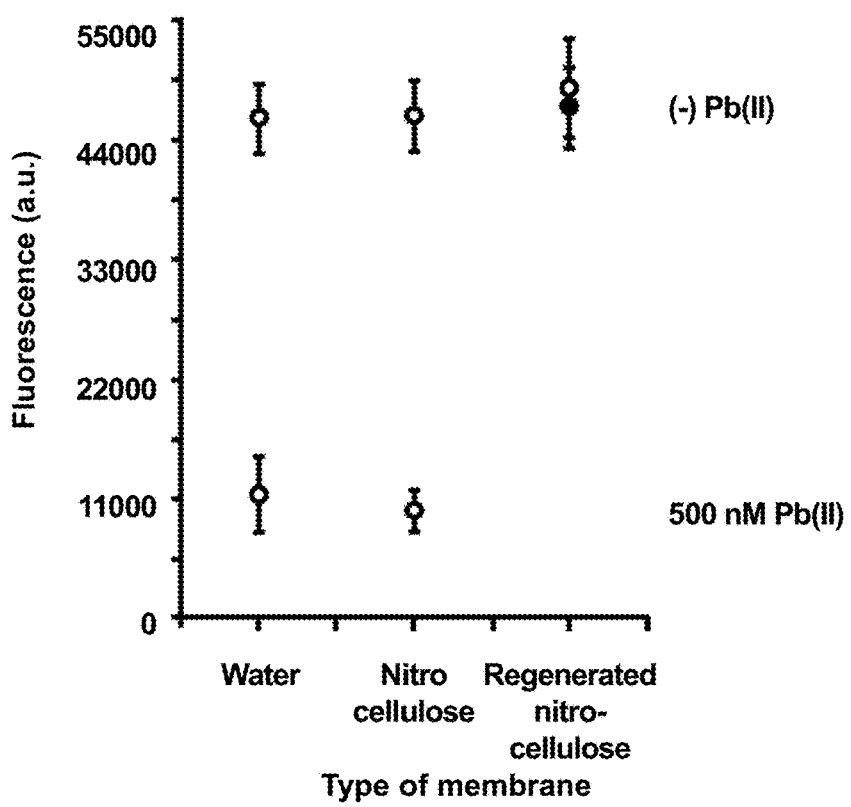
FIG. 4 shows a plot indicating the effectiveness of the type of membrane on extraction of lead ion from milk via fluorescence detection.

Filtration was used to remove proteins and lipids and thus the choice of membrane was limited to polyvinylidene difluoride (PVDF) and nitrocellulose. Both membranes have high protein binding capacity and can be obtained in several pore sizes. Nitrocellulose is suitable for binding low molecular weight proteins. Since, proteinase K digested most of the proteins into smaller fragments, efficient binding of low molecular weight protein was deemed ideal in this case. Among various pore sizes available, 0.2 μm pore size was selected primarily to prevent small peptide fragments to flow through while not clogging the filter. Regenerated nitrocellulose (0.2 μm pore size) was also used; however, no heavy metal ion was detected after sample preparation. This is believed to be primarily due to low protein binding capacity of regenerated nitrocellulose. FIG. 4 shows the effect of type of membrane on extraction. Filtration using regenerated nitrocellulose failed to detect $Pb^{2+}$ ion present in the milk.

Figure 5:
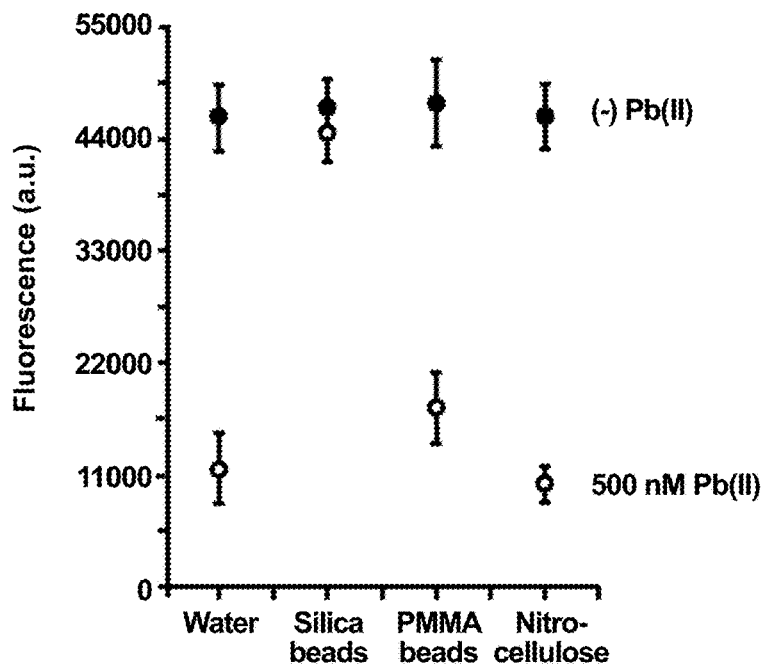
FIG. 5 shows another plot indicating the effectiveness of the type of membrane on extraction of lead ion from milk via fluorescence detection.

As an alternative to nitrocellulose, PMMA and silica beads were also used. These beads are known to adsorb proteins on their surface. However, the signal obtained after extraction via beads indicated that they failed to efficiently remove proteins and lipids. FIG. 5 shows the effect of filtration method on extraction of lead ion from milk. Closed circles indicate fluorescence signal obtained in the absence of lead, whereas open circles indicate fluorescence signal obtained in the presence of 500 nM $Pb^{2+}$. As noted in previous Figures, the result in water was used as a control and to assess the effectiveness of the method.

Additional Combination of Process

Further attempts to simplify the process were made by systematically removing one step at a time. This also allowed assessment of whether each step was absolutely necessary to the overall success.

Figure 6:
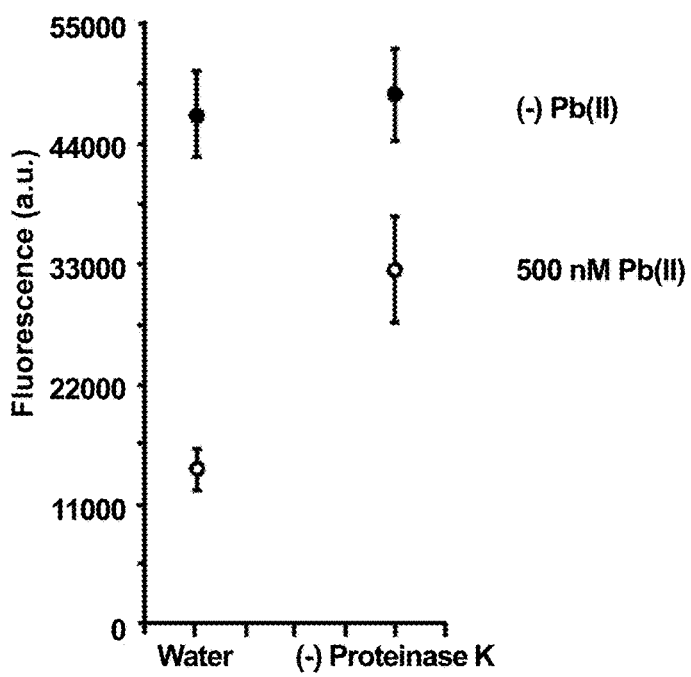
FIG. 6 shows a plot indicating the effectiveness of proteinase K versus a control with no enzyme digestion, on heavy metal extraction from milk via fluorescence detection.

First, proteinase K was removed from the process and the process commenced by adding 167.5 μL of nitric acid (1M) to the diluted milk sample. After filtration through nitrocellulose and an extraction from chloroform, the assay could detect the presence of $Pb^{2+}$ ion in the sample. However, when compared against the control, it was found that the activity was not optimal. FIG. 6 shows the effect of Proteinase K on heavy metal extraction from milk.

Removal of the nitrocellulose filtration from the process was also assessed to determine whether a simple organic extraction is sufficient to remove proteins and lipids. Chloroform was used as the organic solvent and during extraction, a large amount of proteins remain in the interface. Thus, efficient extraction of aqueous layer became an issue and for complete removal, at least five consecutive extractions were required before the aqueous layer could be safely removed without disturbing the interface. This creates complexity and additionally, it was found that the activity of the sensor was sub-optimal. This indicates that the organic solvent extraction without nitrocellulose filtration was not sufficient to remove proteins and lipids.

Process is Independent of Detection Method

Once heavy metal is extracted from the milk, it was detected by DNAzyme-based sensors that are specific to a single metal ion. The detection method for the heavy metals can utilize either fluorescent dyes (Cy3, Cy5, FAM, etc.) or via a GMR method (i.e., magnetic nanoparticles). All the results shown above utilized fluorescent dye Cy3. However, a similar result can be obtained via GMR as shown below.

Overview of the Heavy Metal Extraction Process

In a glass or plastic tube, 1 mL of whole milk was diluted to a final volume of 5 mL with deionized water. 90 μL of proteinase K (0.8 U/μL, New England Biolabs, Ipswich, Mass.) was added to the milk and incubated at room temperature for 15 minutes. After 15 minutes of incubation, 167.5 μL of 1M nitric acid was added to the tube and mixed well to de-emulsify the milk. A 1 mL aliquot of this de-emulsified milk sample was removed using a 1 mL syringe and passed through a nitrocellulose filter (0.2 μm pore size, Maine Engineering). Success of the downstream bioassay depends on the efficient filtration and thus, any white suspension in the filtrate indicates that nitrocellulose filter failed to efficiently remove the proteins and lipids. In such a case, the process was repeated again. The clear filtrate was collected in a 1.5 mL centrifuge tube and the total volume of the filtrate ranged from 200-400 μL, enough for downstream DNAzyme-based assays.

Following filtration, an equal volume of chloroform was added to the filtrate, mixed well and then the tube was allowed to stand for 5 min. The top aqueous layer was carefully removed using a pipette and placed in a new 0.5 mL centrifuge tube. 50 μL of this sample was used for assays to determine the presence of metal ions using functional DNAzyme-based assays as described below. FIGS. 7A and 7B show the quantitative determination of $Pb^{2+}$ and $UO_2^{2+}$ after extraction from milk. The data in the absence of heavy metal ions were obtained by not spiking milk with any heavy metal ion solution.

DNAzyme-Based Assay to Detect Heavy Metals

For assays, DNA microarrays were constructed by immobilizing substrate DNA on a glass slide containing Codelink™ surface (Surmodics, Eden Prairie, Minn.). The substrates were dissolved in a printing buffer containing sodium phosphate and polyvinyl alcohol and arrayed robotically onto glass slides with a distance of 400 μm between the centers of adjacent spots using a piezoelectric spotting robot (Scienion AG, Berlin, Germany). Printing was performed in an enclosed cabinet at about 18° C. and about 70% humidity.

After printing, the microarrays were kept in a humid chamber at room temperature for about 12 to 16 hours. The substrates were immobilized on glass slides via a reaction between NHS ester group on the surface and 3'-terminal primary amine on the substrates. The excess functional groups on the slide were blocked using a solution of 50 mM ethanolamine. Following the blocking with ethanolamine, the slides were washed with de-ionized water and spin-dried. The microarrays were generated so that there were twelve sub-arrays per glass slide and sub-arrays were separated by placing a polystyrene ring around each sub-array. This process created twelve reaction chambers per slide.

DNAzyme sensors, 1000-fold in excess over immobilized substrate, were dissolved in reaction buffer, 85 μL of the solution was added to the reaction chamber and the reaction was initiated by adding 0.85 μL of heavy metal ion solution. The reaction was allowed to proceed for 15 minutes and then the solution was removed from the reaction chamber via pipette. The reaction chamber was washed twice with 85 μL of reaction buffer to remove residual cleaved substrate and excess DNAzyme sensor.

To detect using fluorescence, to the reaction chamber 90 μL of Cy3-streptavidin dye (5 μg/mL in reaction buffer) was added and incubated at room temperature for 30 minutes. Following removal of the dye, the slides were washed with 0.5% sodium dodecyl sulfate solution and de-ionized water. The slides were imaged on the Axon GenePix 4000B (Axon Instruments, Foster City, Calif.) scanner with 5 μm resolution using a Cy5/Cy3 optical filter. The laser power and photomultiplier tube voltage (PMT) were set to gain optimum signal intensities. The original 16-bit tiff images were quantified with GenePix software 6.0 (Axon Instruments, Foster City, Calif.). To detect using GMR, to the reaction chamber 80 μL of streptavidin coated magnetic nanoparticle was added and signal detected and recorded using a GMR device. FIGS. 8A and 8B show the detection of lead and uranium using the GMR sensors.

What is claimed is:

1. A kit comprising:
   a container for holding a protein-containing sample;
   proteinase K;
   concentrated nitric acid;
   chloroform;
   a handheld device for detecting metal ions, the handheld device employing detection based on giant magnetoresistance; and
   instructions for performing the isolation of metal ions from the protein-containing sample.

2. The kit of claim 1, wherein the kit is a small scale kit for performing the isolation of metal ions in the field.

3. The kit of claim 1, further comprising other protein denaturing agents.

4. The kit of claim 3, wherein the further protein denaturing agents comprise at least one selected from the group consisting of sodium dodecyl sulfate (SDS), urea, ethylenediamine tetraacetic acid, trypsin, and chymotrypsin.

\* \* \* \* \*